United States Patent [19]
Shimotoso et al.

[11] Patent Number: 6,010,336
[45] Date of Patent: *Jan. 4, 2000

[54] LIVING BODY-SUPPORTING MEMBER AND PREPARATION PROCESS THEREOF

[75] Inventors: Toshihiko Shimotoso; Akira Terui; Hiroyuki Kitano, all of Shiga, Japan

[73] Assignee: Kyocera Corporation, Kyoto, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/580,018

[22] Filed: Dec. 20, 1995

[30] Foreign Application Priority Data

Dec. 26, 1994 [JP] Japan ................................ 6-323202

[51] Int. Cl.⁷ .................................................. A61F 27/00
[52] U.S. Cl. ...................................... 433/201.1; 623/16
[58] Field of Search ........................ 433/173, 201.1; 623/16; 606/76, 77

[56] References Cited

U.S. PATENT DOCUMENTS

| | | | |
|---|---|---|---|
| 4,990,163 | 2/1991 | Ducheyne et al. | 623/16 |
| 5,108,432 | 4/1992 | Gustavson | 623/16 |
| 5,141,510 | 8/1992 | Takagi et al. | 433/201.1 |
| 5,222,987 | 6/1993 | Jones | 623/16 |
| 5,348,788 | 9/1994 | White | 623/16 |
| 5,380,328 | 1/1995 | Morgan | 623/16 |
| 5,455,100 | 10/1995 | White | 623/16 |
| 5,496,372 | 3/1996 | Hamamoto et al. | 623/16 |
| 5,507,814 | 4/1996 | Gilbert et al. | 623/16 |
| 5,531,794 | 7/1996 | Takagi et al. | 623/16 |

FOREIGN PATENT DOCUMENTS 6007388   1/1994   Japan ......................... 623/16

*Primary Examiner*—Ralph A. Lewis
*Attorney, Agent, or Firm*—Loeb & Loeb, LLP

[57] ABSTRACT

A living body-supporting member having a surface layer with multiple pores regularly arranged therein, in which the porous portions constituting the living body-supporting member are made of ceramics giving no harm to a human body. And a method to perforate multiple pores in a green sheet made of the ceramics, to laminate the green sheets so that pores communicate with each other, and to fire it. The living body-supporting member is coupled with the bone, and there is no risk that it may drop from the supporting portion. Even if the substrate is composed of ceramics, the substrate and the surface layer can be integrally coupled with each other, thereby there is no risk that both of them are separated. Furthermore, according to the above method, the pore shapes of the porous body can be preliminarily designed so that pores communicate with each other while being displaced for every certain depth, and it can be accurately controlled in the production thereof.

13 Claims, 4 Drawing Sheets

LIVING BODY-SUPPORTING MEMBER AND PREPARATION PROCESS THEREOF

FIELD OF THE INVENTION

The present invention relates to a living body-supporting member which constitutes an artificial root of a tooth or the like or is used for reconstruction of bone functions and joints of limbs lost due to disease or disaster, or teeth lost due to old age or disease, and the preparation process thereof.

BACKGROUND OF THE INVENTION

As the above-mentioned artificial supporting member having a porous body, there has been proposed a supporting member made of metal or ceramic.

As an artificial supporting member made of metal, there has been proposed, for example, an artificial operating member made of metal which is obtained by sintering and fixing beads made of metal on the surface thereof, obtained by forming a porous body on the surface thereof by casting, or obtained by laminating several mesh sheets.

On the other hand, as one made of ceramic, there has been proposed a method in which organic materials such as organic resin powders and organic fibers are dispersed in the ceramic raw material at the time of preparation of the raw materials, and three-dimensional net-like organic materials are blended into the inside of the mold by firing, and after forming, the organic portion is oxidized and eliminated by dry firing to obtain the porous material.

However, in the conventional art, there have been problems such as those described below.

Namely, none of the conventional art can accurately control the shape of the pores, other than the one which laminates several mesh sheets, therefore the pore shapes may be different for every product, or they cannot optimally lead the bone to reproduce and penetrate.

On the other hand, while the mesh sheet multilayer type can accurately control the pore shape so that it can optionally lead the bone to reproduce and penetrate, since it is composed of metal there is a problem in integration with the ceramic materials. Therefore, there have been problems such that the bone drops out from the ceramic substrates. Even if it does not drop out therefrom, the micro-movement due to the slackness between substrates has a negative influence on the living body, or it may affect the abrasiveness of the sliding face.

SUMMARY OF THE INVENTION

The present invention solves the above problems by making the porous body constituting the living body-supporting member with ceramics giving no harm to the living body and forming multiple pores communicating with each other while being displaced for every certain depth.

As a method to obtain such a porous body, a lamination technique of the ceramic package is applied. Namely, there is provided a method in which multiple pores are perforated in a green sheet of the ceramic material, and the green sheet is optionally laminated so that pores communicate with each other, then it is fired.

By laminating and integrally sintering the unfired thin plate in which multiple pores or slits are perforated, while displacing the position of pores perforated in the thin plate at certain depths, a porous body can be obtained in which the micro pores communicate three-dimensionally, and the circulation state of the micro pores is properly controlled. This porous body can be used directly as the living body-supporting member, or it may be coupled to the surface of substrates constituting the living body-supporting member by integral sintering or bonding, to become the surface of the living body-supporting member. And, by embedding this living body supporting member into the bone, the new bone reproduces and penetrates into pores which constitute the three-dimensional structure, and the bone structure can strongly hold the living body supporting member in the living body by means of its solid structure.

Furthermore, by constituting a dense portion which is the substrate by zirconia or alumina and the porous portion by calcium phosphate-type ceramics, reproduction of the bond to the porous portion can be further promoted. Thus, the fixation with bone at an earlier stage can be made possible.

In addition, it is desirable if the certain depth is between about 100 to 1000 $\mu$m. This is because this range is most suitable to promote the reproduction of the new bone into micro pores. If the certain depth becomes larger than about 1000 $\mu$m, the effective diameter of pores at the time of lamination becomes too large to hinder the reproduction of the new bone into micro pores. On the other hand, if it is smaller than about 100 $\mu$m, the effective diameter of pores becomes too small to cause similar problems. Furthermore, when the certain depth is not larger than 100 $\mu$m, the strength of the porous portion may become weak. Thus, it is not suitable for an application where a large load is given.

BRIEF DESCRIPTION OF THE DRAWINGS

A detailed description of the preferred embodiments of the present invention will be made with reference to the accompanying drawings.

DETAILED DESCRIPTION OF THE PREFERRED EMBODIMENTS

EXAMPLES

Examples of the present invention will now be described in detail with reference to the accompanying drawings.

Example 1

Figure 1:
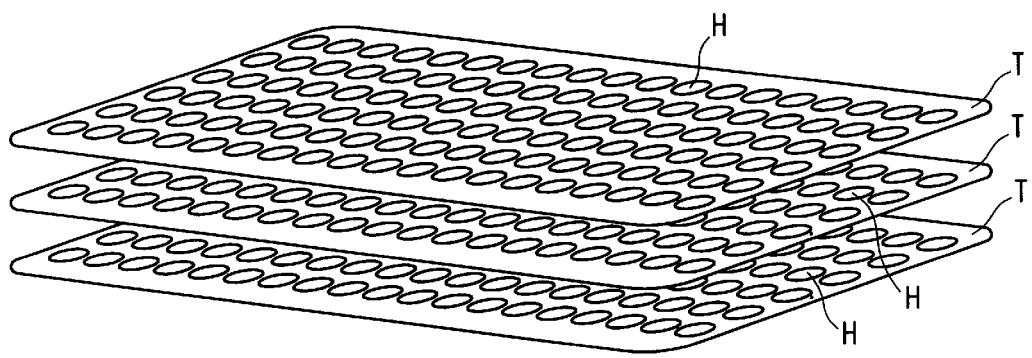
FIG. 1 shows an example of a perspective view showing a tape (green sheet) laminated at the time of production the living body-supporting member in an example of the present invention.
Figure 2:
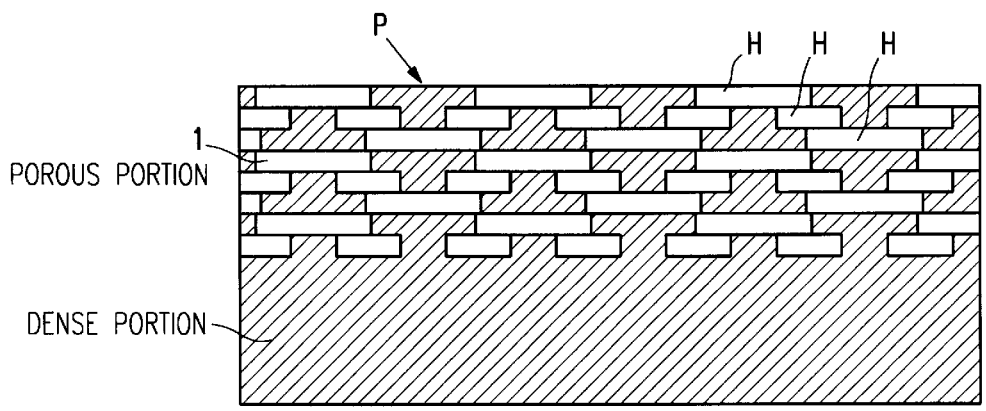
FIG. 2 shows an example of a longitudinally sectional view of the living body-supporting member in an example of the present invention.

To 100% by weight of alumina powder having an average particle diameter of 0.4 $\mu$m were added 0.3% by weight of dispersing material, 8% by weight of organic binder, 0.2% by weight of antifoaming agent, and 25% of water was added thereto to adjust a slip, which was used to prepare a tape having a thickness of 0.3 mm by a doctor blade method. This tape was cut to a desired size, and perforated by punching. There are two types of pore patterns, and one type is such that circular pores having a diameter of 1.0 mm are perforated at 1.5 mm pitches. Another type is that circular pores having a diameter of 2.0 mm are perforated at 3 mm pitches. These two types of tapes T were alternately laminated up to 8 layers so that pores H could be communicated with each other as shown in FIG. 1 to form a porous body. Next, this porous body was bonded to a plate materials cut from a rubber press molded body which had the same quality of the material with that of this tape, and dried and fired at a temperature of 1550° C. in an oxidizing atmosphere, thus the living body-supporting member P of the present invention which was a two-layer structure comprising a surface layer composed of porous portions 1 and a parent material composed of dense portions as shown in FIG. 2 was obtained.

Figure 3:
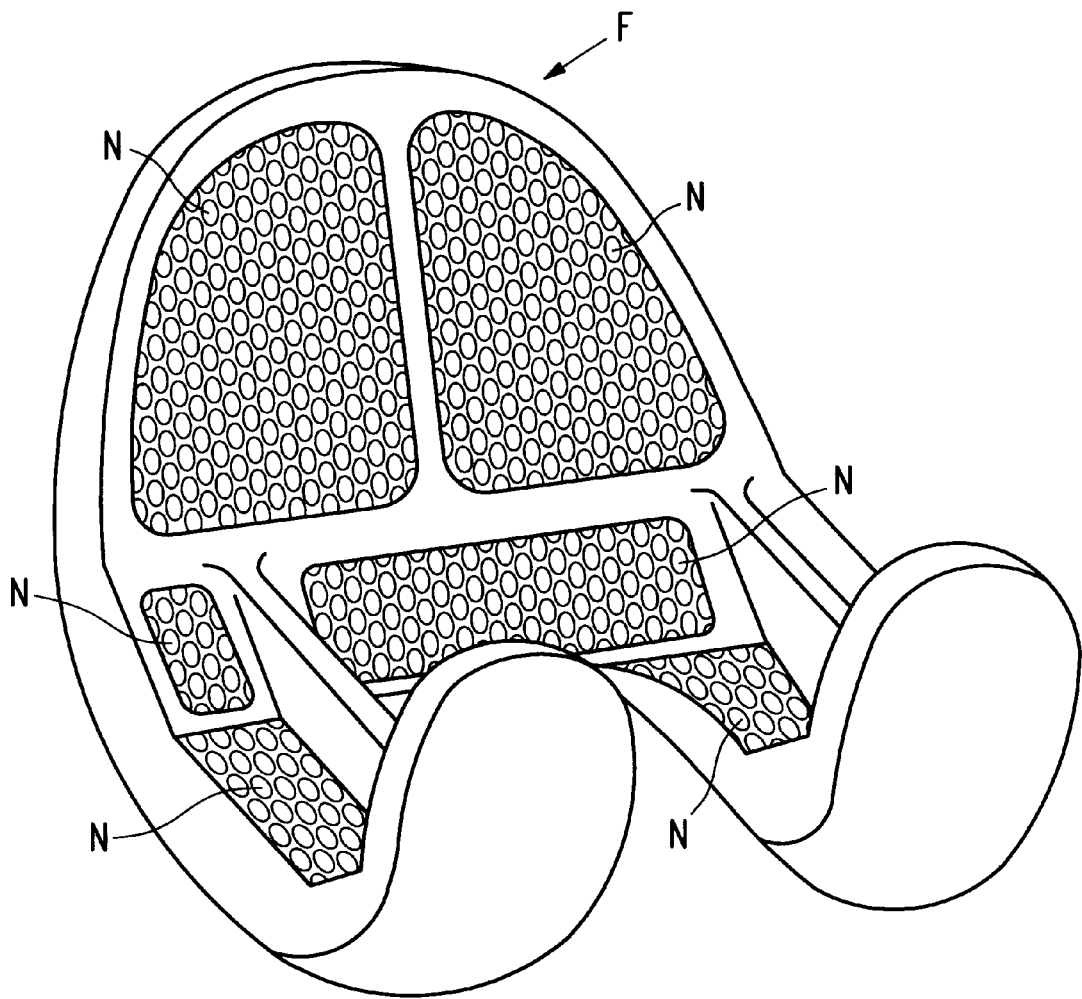
FIG. 3 shows an example of a perspective view of a femur component of an artificial knee as the living body-supporting member in an example of the present invention.

FIG. 3 shows femur component F of an artificial knee with porous body N bonded thereto prepared by the above-mentioned method.

Figure 4:
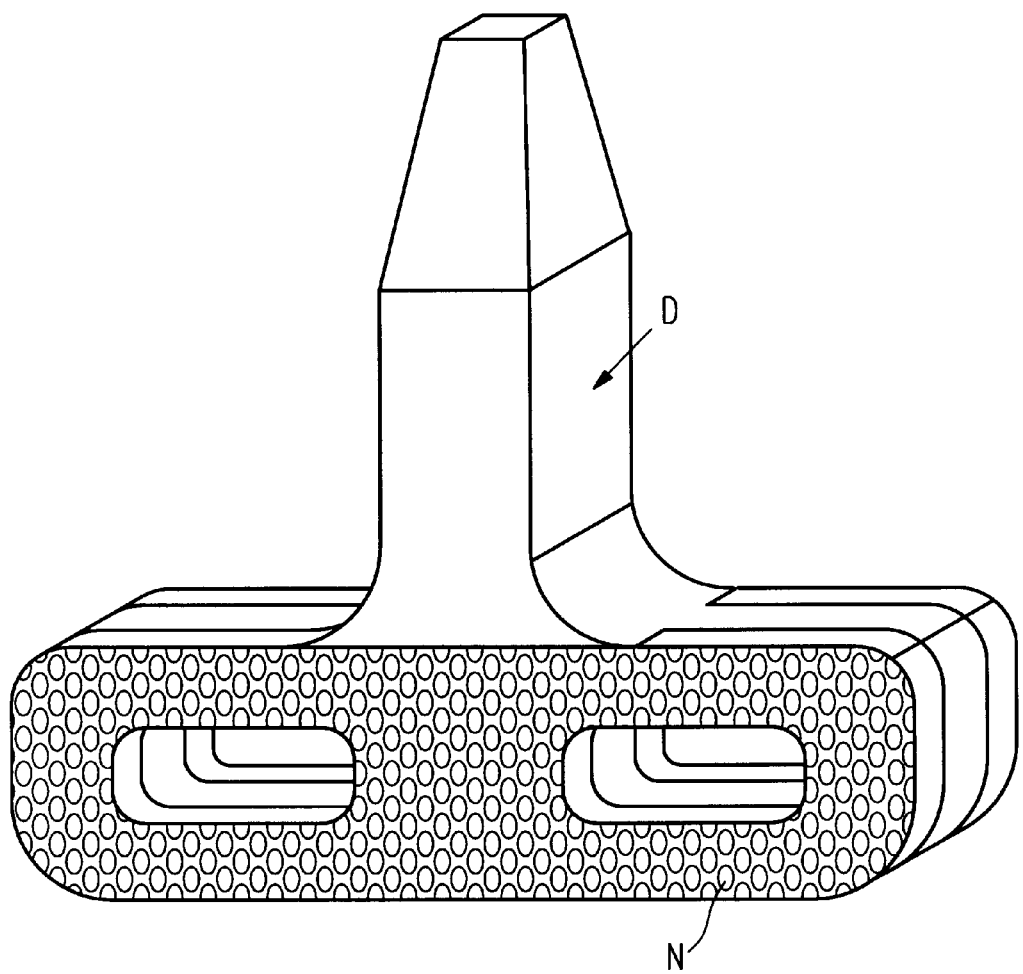
FIG. 4 shows an example of a perspective view of an artificial root of tooth as the living body-supporting member in an example of the present invention.

Furthermore, FIG. 4 shows a ceramic implant D for dental applications with porous body N bonded to a bone-embedded portion prepared by the above-mentioned method.

Example 2

Figure 5:
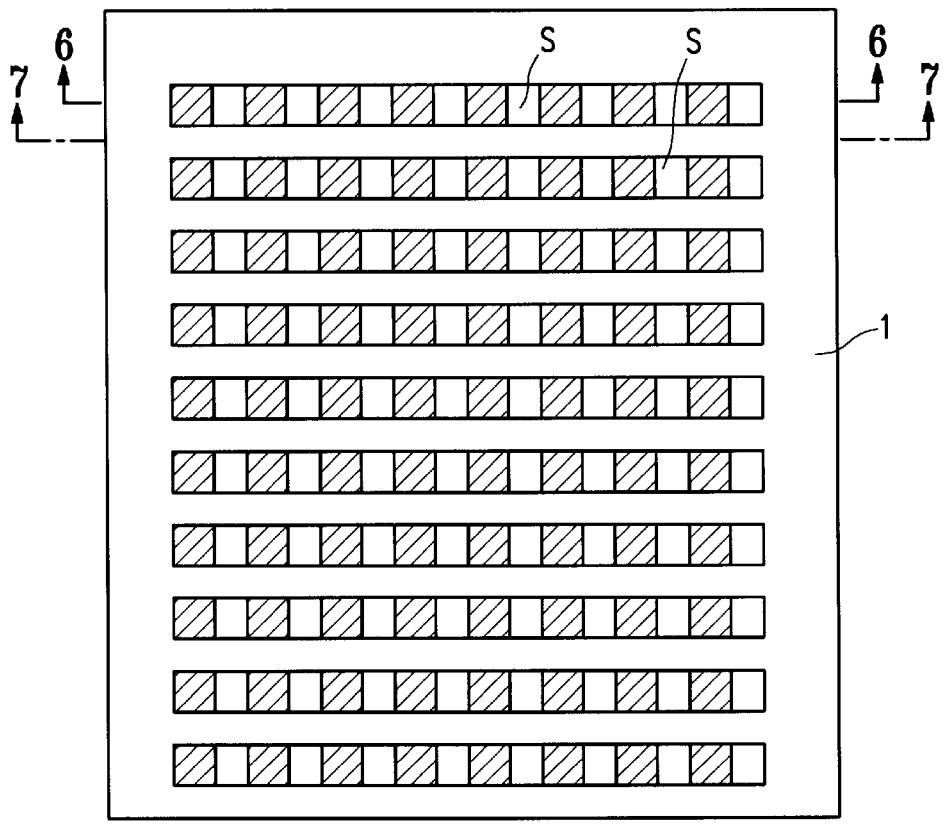
FIG. 5 is a plan view of the porous portion constituting the living body-supporting member in an example of the present invention.
Figure 6:
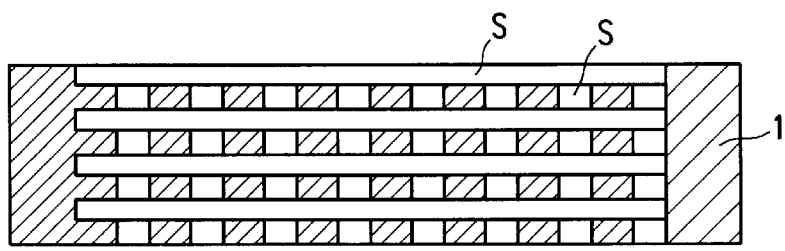
FIG. 6 shows an example of a sectional view along the line A—A of FIG. 5.
Figure 7:
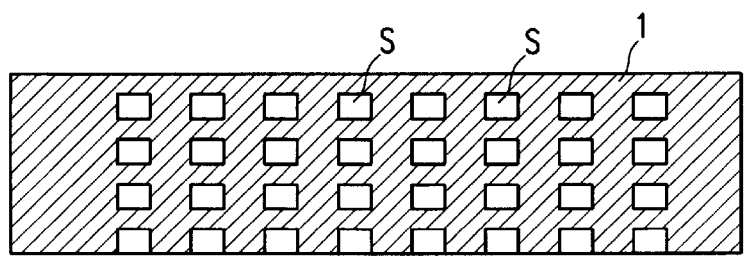
FIG. 7 shows an example of a sectional view along the line B—B of FIG. 5.

To 100% by weight of zirconia power having an average particle diameter of 0.6 μm were added 0.5% by weight of dispersing material, 10% by weight of organic binder, 0.5% by weight of antifoaming agent, and 25% of water was added thereto to prepare slip, which was used to prepare a tape having a thickness of 0.5 mm by a doctor blade method. This tape was cut to a desired size, and punched with a mold so that slits of 0.5 mm were made at 1 mm pitches. This tape was alternately laminated up to 8 layers so that slits S were orthogonal to form a porous body. Next, this porous body was bonded to a plate material cut from a zirconia rubber press molded body which had the same quality of the material with that of this tape, and fired at a temperature of 1450° C. in an oxidizing atmosphere, thus the living body-supporting ember comprising porous portions 1 and dense portions was obtained. FIGS. 5–7 show the structure of porous portions 1 of this living body-supporting member.

Example 3

To 100% by of apatite powder having an average diameter of 1 μm were added 1.0% by weight of dispersing material, 5% by weight of organic binder, 0.5% by weight of antifoaming agent, and 20% of water was added thereto to prepare a slip, which was used to prepare a tape having a thickness of 0.05 mm by a doctor blade method. This tape was subjected to punching as in Example 1 and laminated up to 20 layers so that pores could communicate with each other, to obtain a porous body. This porous body was fired at a temperature of 1300° C. in an oxidizing atmosphere, thus the living body-supporting member composed of apatite was obtained.

Example 4

To 100% by weight of zirconia powder having a average particle diameter of 0.6 μm were added 0.8% by weight of dispersing material, 5% by weight of organic binder, 0.5% by weight of antifoaming agent, and 30% of water was added thereto to prepare a slip, which was used to prepare a thin plate of 40×50×0.06 mm by a cast molding method. One type is such that this thin plate was subjected to punching to make circular pores having a diameter of 0.5 mm at 1.0 mm pitches. Another type is such that circular pores having a diameter of 0.5 mm were punched at 1.0 mm pitches. These two types of thin plates were alternatively laminated up to 8 layers so that pores could communicate with each other to form a porous body. This porous body was bonded to the cast molded body prepared by the slip, dried, and fired at a temperature of 1450° C. in an oxidizing atmosphere.

Example 5

To 100% by weight of apatite powder having an average particle diameter of 1 μm were added 1.0% by weight of dispersing material, 5% by weight or organic binder, 0.5% by weight of antifoaming agent, and 20% of water was added thereto to prepare a slip, which was used to prepare a tape having a thickness of 0.5 mm by a doctor blade method. This tape was subjected to punching to make circular pores as in Example 1 and laminated up to 8 layers so that the pores could communicate with each other to obtain a porous body.

Furthermore, a plate material was prepared by a cast molding method, by using an ultra-fine alumina raw material having a temporary diameter of 0.1 μm and an average particle diameter of 0.3 μm, whose firing temperature was 1300° C. The apatite body was bonded to this alumina molded body, which was dried and fired at a temperature of 1300° C. in an oxidizing atmosphere, thus the living body-supporting member which was an integrally fired two-layer structure comprising a surface layer composed of apatite porous portions 1 and a parent material composed of alumina dense portions.

In addition, the range of the present invention is not Limited by these examples, and the thickness of laminated green sheets may not be fixed, and may be optionally changed so far as it does not depart from the object of the present invention.

As described above, in porous portions constituting the surface layer of the living body-supporting member of the present invention, by forming multiple pores communicating with each other, while being displaced for every roughly certain depth, the bone reproduces and penetrates densely, thereby the living body-supporting member is coupled with the bond strongly so that there is no risk that it drops out from the supporting portion. Furthermore, by constituting the porous body with ceramics, even if the substrate is composed of ceramics, the substrate and the porous body can be integrally coupled with each other, thereby there is no risk that both of them can be separated. Furthermore, when the sliding face is composed of ceramics, the abrasiveness becomes excellent by the effect of the integral coupling.

In addition, in obtaining such living body-supporting member, the present invention applies the multilayer technique of ceramics and also provides a method to perforate multiple pores in the green sheet of ceramic materials, to optionally laminate the green sheets so that the pores communicate with each other, and to fire it. According to this method, such an excellent effect can be exerted that the pore shapes of the porous body can be preliminarily designed so that the pores communicate with each other while being displaced for every certain depth, and it can be accurately controlled in the production thereof.

What is claimed is:

1. A process of preparing a living body supporting member, comprising:

providing a plurality of green sheets of biologically inert ceramic material, each of the plurality of green sheets having a thickness between about 100 and 1000 microns, perforating each of the plurality of green sheets with a plurality of regularly spaced pores, laminating the plurality of green sheets so that the plurality of regularly spaced pores of each green sheet is displaced relative to the plurality of regularly spaced pores of at least one adjacent green sheet and the plurality of regularly spaced pores of each green sheet communicates with the plurality of regularly spaced pores of at least one adjacent green sheet, and firing the laminated plurality of green sheets.

2. A process of preparing a living body supporting member according to claim 1, further comprising a step of bonding the plurality of laminated green sheets to a plate of biologically inert ceramic material thicker than each of the plurality of green sheets.

3. A process of preparing a living body supporting member according to claim 2, wherein the plate and the plurality of laminated green sheets use the same biologically inert ceramic material.

4. A process of preparing a living body supporting member according to claim 3, further comprising a step of firing the plurality of laminated green sheets bonded to the plate to form a two-layer structure including a porous portion formed from the plurality of laminated green sheets and a dense portion formed from the plate.

5. A process of preparing a living body supporting member according to claim 1, further comprising:

a step of dividing the plurality of green sheets into first and second groups;

a step of perforating each of the green sheets in the first group with first pores at a first pitch, each of the first pores having a first diameter;

a step of perforating each of the green sheets in the second group with pores at a second pitch greater than the first pitch, each of the second pores having a second diameter; and a step of alternately laminating the perforated green sheets in the first group and the perforated green sheets in the second group.

6. A process of preparing a living body supporting member according to claim 5, wherein the second diameter is greater than the first diameter.

7. A process of preparing a living body supporting member according to claim 6, further comprising a step of bonding the plurality of laminated green sheets to a plate of biologically inert ceramic material thicker than each of the plurality of green sheets.

8. A process of preparing a living body supporting member according to claim 7, wherein the plate and the plurality of laminated green sheets use the same biologically inert ceramic material.

9. A process of preparing a living body supporting member according to claim 8, further comprising a step of firing the plurality of laminated green sheets bonded to the plate to form a two-layer structure including a porous portion formed from the plurality of laminated green sheets and a dense portion formed from the plate.

10. A process of preparing a living body supporting member, comprising:

providing a plurality of green sheets of biologically inert ceramic material, each of the plurality of green sheets having a thickness between about 100 and 1000 microns, perforating each of the plurality of green sheets with a plurality of regularly spaced slits, laminating the plurality of green sheets so that the plurality of regularly spaced slits of each green sheet is disposed transverse with respect to the plurality of regularly spaced slits of at least one adjacent green sheet and the plurality of regularly spaced slits of each green sheet communicates with the plurality of regularly spaced slits of at least one adjacent green sheet, and firing the laminated plurality of green sheets.

11. A process of preparing a living body supporting member according to claim 10, wherein the regularly spaced slits of each of the plurality of green sheets are perforated to extend across substantially the width of each of the plurality of green sheets.

12. A process of preparing a living body supporting member according to claim 11, wherein the plurality of green sheets are laminated so that the plurality of regularly spaced slits of each green sheet is disposed transverse with respect to the plurality of regularly spaced slits of an adjacent green sheet.

13. A process of preparing a living body supporting member according to claim 10, further comprising a step of bonding the plurality of laminated green sheets to a plate of biologically inert ceramic material thicker than each of the plurality of green sheets.

* * * * *